United States Patent [19]
Faubert et al.

[11] Patent Number: 5,919,132
[45] Date of Patent: Jul. 6, 1999

[54] ON-LINE AND REAL-TIME SPECTROREFLECTOMETRY MEASUREMENT OF OXYGENATION IN A PATIENT'S EYE

[75] Inventors: Jocelyn Faubert, Notre-Dame-de-l'Ile-Perrot; Vasile Diaconu, Ile Perrot, both of Canada

[73] Assignee: Universite de Montreal, Quebec, Canada

[21] Appl. No.: 09/048,721

[22] Filed: Mar. 26, 1998

[51] Int. Cl.[6] .................................................. A61B 5/00
[52] U.S. Cl. .................... 600/318; 600/340; 600/473; 600/476
[58] Field of Search .................... 600/318, 320, 600/322, 323, 340, 473, 476; 606/2, 3, 4, 5, 6, 10, 11, 13, 17, 18

[56] References Cited

U.S. PATENT DOCUMENTS

| | | | |
|---|---|---|---|
| 4,253,744 | 3/1981 | Sawa | 351/16 |
| 4,305,398 | 12/1981 | Sawa | 128/633 |
| 4,413,890 | 11/1983 | Belkin et al. | 351/221 |
| 4,485,820 | 12/1984 | Flower | 128/633 |
| 4,569,354 | 2/1986 | Shapiro et al. | 128/665 |
| 4,579,430 | 4/1986 | Bille | 351/206 |
| 4,621,643 | 11/1986 | New, Jr. et al. | 128/633 |
| 4,644,948 | 2/1987 | Lang et al. | 128/303.1 |
| 4,770,179 | 9/1988 | New, Jr. et al. | 128/633 |
| 4,877,322 | 10/1989 | Hill | 351/221 |
| 4,922,919 | 5/1990 | Novack | 128/633 |
| 5,069,214 | 12/1991 | Samaras et al. | 128/633 |
| 5,090,416 | 2/1992 | Ogino et al. | 128/691 |
| 5,119,814 | 6/1992 | Minnich | 128/633 |
| 5,186,173 | 2/1993 | Zuckerman | 128/633 |
| 5,219,400 | 6/1993 | Jacot et al. | 128/633 |
| 5,240,006 | 8/1993 | Fujii et al. | 128/665 |
| 5,308,919 | 5/1994 | Minnich | 128/633 |
| 5,318,022 | 6/1994 | Taboada et al. | 128/633 |
| 5,433,197 | 7/1995 | Stark | 128/633 |
| 5,553,617 | 9/1996 | Barkenhagen | 600/318 |
| 5,582,168 | 12/1996 | Samuels et al. | 128/633 |
| 5,608,526 | 3/1997 | Piwonka-Corle et al. | 356/369 |
| 5,673,097 | 9/1997 | Heacock | 351/218 |

OTHER PUBLICATIONS

Dietrich Schweitzer, Lutz Leistritz, Martin Hammer, Mateusz Scibor, Ulrich Bartsch and Jurgen Strobel; "Calibration–free measurement of the oxygen saturation in retinal vessels of men"; *SPIE*; vol. 2393, pp. 210–218.

"Ocular Hazards from Clinical Instruments" D.G. Pitts, R.N. Kleinstein, Environmental Vision, Interactions of the Eye, Vision, and the Environment, pp. 379–386.

"Imaging Spectrometry in Ophthalmology—Principle and Application in Microcirculation and in Investigation of Pigments" D.Schweitzer et al, Ophthalmic Res 1996, pp. 37–44.

*Primary Examiner*—Gary E. O'Connor
*Assistant Examiner*—Eric F. Winakur
*Attorney, Agent, or Firm*—Merchant, Gould, Smith, Edell, Welter & Schmidt

[57] ABSTRACT

In the spectroreflectometry oxygenation measuring method and device, a light source produces a light beam having a spectral bandwidth including the wavelengths from 450 nm to 850 nm. A first optical system propagates the light beam from the light source to the fundus of a patient's eye, the light beam being reflected at least in part by the fundus of the patient's eye to produce a reflected light beam. A detector unit detects the spectral content of the reflected light beam and produces a signal indicative of this spectral content. A second optical system propagates an axial central portion of the reflected light beam along a predetermined propagation path from the fundus of the patient's eye to the detector unit. To that effect, the second optical system comprises a mirror defining an angle of 45° with the predetermined propagation path and comprising (a) an axial opening for transmitting to the detector unit only the axial central portion of the reflected light beam, and (b) a light-reflecting surface surrounding the axial opening for deviating the axial peripheral portion of the reflected light beam toward the display system. The detector unit comprises a spectrograph responsive to the axial central portion of the reflected light beam to produce a light spectrum, and an array of detectors for measuring intensities of the light components of different wavelengths of the light spectrum. The light beam from the light source has an intensity substantially equal to daylight.

19 Claims, 4 Drawing Sheets

ON-LINE AND REAL-TIME SPECTROREFLECTOMETRY MEASUREMENT OF OXYGENATION IN A PATIENT'S EYE

BACKGROUND OF THE INVENTION

1. Field of the Invention

The present invention relates to a method and device for conducting on-line and real-time spectroreflectometry oxygenation measurement in the eye.

2. Brief Description of the Prior Art

A known prior art method uses a xenon flash, a fundus camera and a CCD (Charge Coupled Device) detector to make spectrographic measurements of the fundus of the eye. The xenon flash illuminates the eye during a short period of time for a single measurement. Due to the high intensity of the xenon light, such measurement could not be repeated on a continuous basis without harming the eye.

For measuring the oxygen content of blood, other prior art methods perform blood flow measurements using Doppler based procedures.

Another prior art method is described in U.S. Pat. No. 4,569,354 (Shapiro et al.) issued on Feb. 11, 1986. In accordance with this method, oxygenation of the retina is determined by measuring the fluorescence of flavoprotein in the retina. A spot of excitation light of a frequency of about 450 nanometers is scanned across the retina. Fluorescent light emitted from the retina at a frequency of about 520 nanometers is detected. The emission light may be detected at two frequencies of about 520 nm and 540 nm to allow for compensation for absorption and transmission variables in the eye. The center of the lens is imaged onto an optical stop in the emission optical path so that emitted light which passes back through the lens periphery, and not fluorescent light from the center of the lens, is detected.

U.S. Pat. No. 5,433,197 granted to Edward W. Stark on Jul. 18, 1995 discloses a glucose sensor for determining blood glucose which is of particular value in the diagnosis and treatment of diabetes. The patient's eye is illuminated with near-infrared radiation which passes into the eye through the cornea and the aqueous humor, is reflected from the iris and/or lens surface, and then passes out through the aqueous humor and cornea. The reflected radiation is collected and detected by a near-infrared sensor which measures the reflected energy in one or more wavelength bands. Comparison of the reflected energy with the source energy provides a measure of the spectral absorption by the eye which is characteristic of the composition of the cornea, the aqueous humor, and the other structures within the eye through which the energy is transmitted or from which it is reflected.

The above prior art evidences that need still exists for an efficient method and device for performing on-line and real-time oxygenation measurement in the eye.

OBJECTS OF THE INVENTION

A general object of the present invention is to conduct on-line and real-time spectroreflectometry oxygenation measurement in a patient's eye.

Another object of the present invention is to provide a method and device using the axial central portion of a light beam reflected from the fundus of a patient's eye to make a spectroreflectometry oxygenation measurement in the eye, the use of the axial central portion of the reflected light beam enabling selection of a small precise area which is optimal for oxygenation measurement of specific structures such as the blindspot, arteries, veins, etc.

A further object of the present invention is to provide a method and device transmitting the axial peripheral portion of the reflected light beam to a display system enabling an operator to visualize the fundus of the patient's eye and the location of the light beam on the fundus of the patient's eye without positioning error.

A still further object of the present invention is to provide a method and device using an optimal spectral bandwidth for performing in the patient's eye a spectroreflectometry measurement of hemoglobin and its derivatives such as oxyhemoglobin and carbonylhemoglobin.

SUMMARY OF THE INVENTION

More specifically, in accordance with the present invention, there is provided a spectroreflectometry oxygenation measuring method comprising the steps of producing a light beam having a predetermined spectral bandwidth by means of a light source, propagating the light beam toward a region of the fundus of a patient's eye, reflecting at least in part the light beam on the fundus of the patient's eye to produce a reflected light beam having a geometrical longitudinal axis, by means of a detector unit detecting the spectral content of the reflected light beam and producing a signal indicative of the spectral content of this reflected light beam, and propagating the reflected light beam along a predetermined propagation path from the fundus of the patient's eye to the detector unit. The step of propagating the reflected light beam comprises transmitting to the detector unit only an axial central portion of the reflected light beam corresponding to a small precise area of the fundus of the patient's eye where a spectroreflectometry oxygenation measurement is desired.

In accordance with a preferred embodiment, the reflected light beam comprises an axial peripheral portion surrounding the axial central portion, and the step of propagating the reflected light beam further comprises transmitting the axial peripheral portion of the reflected light beam to a display system enabling an operator to visualize the fundus of the patient's eye and the location of the light beam on the fundus of the patient's eye.

The present invention also relates to a spectroreflectometry oxygenation measuring device, comprising a light source, a first optical system, a detector unit, and a second optical system. The light source produces a light beam having a predetermined spectral bandwidth, and the first optical system propagates the light beam from the light source to a region of the fundus of a patient's eye, the light beam being reflected at least in part by the fundus of the patient's eye to produce a reflected light beam having a geometrical longitudinal axis. The detector unit detects the spectral content of the reflected light beam and produces a signal indicative of the spectral content of that reflected light beam. The second optical system propagates the reflected light beam along a predetermined propagation path from the fundus of the patient's eye to the detector unit. Finally, the second optical system comprises means for transmitting to the detector unit only an axial central portion of the reflected light beam corresponding to a small precise area of the fundus of the patient's eye where a spectroreflectometry oxygenation measurement is desired.

In accordance with a preferred embodiment, the reflected light beam comprises an axial peripheral portion surrounding the axial central portion, and the second optical system transmits the axial peripheral portion of the reflected light beam to a display system enabling an operator to visualize the fundus of the patient's eye and the location of the light beam on the fundus of the patient's eye.

Preferably, the predetermined spectral bandwidth includes wavelengths located in a range comprises between 450 nm and 850 nm.

In accordance with other preferred embodiments of the invention:

to transmit to the detector unit only an axial central portion of the reflected light beam, an axial opening is formed in a mirror defining an angle of 450 with the predetermined propagation path, this axial opening having a predetermined diameter centered on the geometrical longitudinal axis of the reflected light beam;

the mirror comprises a light-reflecting surface surrounding the axial opening to deviate the axial peripheral portion of the reflected light beam toward the display system;

the detector unit comprises:
 a spectrograph responsive to the axial central portion of the reflected light beam to produce a dispersion of the light in which light components of the axial central portion of the reflected light beam are arranged in order of wavelengths; and
 an array of detectors for measuring intensities of the light components of different wavelengths of the light spectrum;

the spectroreflectometry oxygenation measuring device further comprises a computer station responsive to the measured intensities of the light components of different wavelengths of the light spectrum for computing and displaying a graph of absorbance of the small precise area of the fundus of the patient's eye as a function of wavelength within the predetermined spectral bandwidth;

the spectroreflectometry oxygenation measuring device comprises a portable fundus camera incorporating the light source, the first optical system and a portion of the second optical system, and the second optical system further comprises an optical fiber for transmitting the axial central portion of the reflected light beam from the portable fundus camera to the detector unit;

the display system displays an image of the fundus of the patient's eye including a black spot indicating the region of the fundus of the patient's eye to which the light beam from the light source is applied, and the black spot is produced by the axial opening of the mirror and corresponds to the axial central portion of the reflected light beam transmitted to the detector unit; and the light beam produced by the light source has an adjustable intensity which at its maximum level is still sufficiently low for being applied to the fundus of the patient's eye for the duration of the spectroreflectometry oxygenation measurement while causing no harm to the patient's eye; preferably, the light beam from the light source has an intensity substantially equal to daylight.

The objects, advantages and other features of the present invention will become more apparent upon reading of the following non restrictive description of preferred embodiments thereof, given by way of example only with reference to the accompanying drawings.

DETAILED DESCRIPTION OF THE PREFERRED EMBODIMENT

Figure 1:
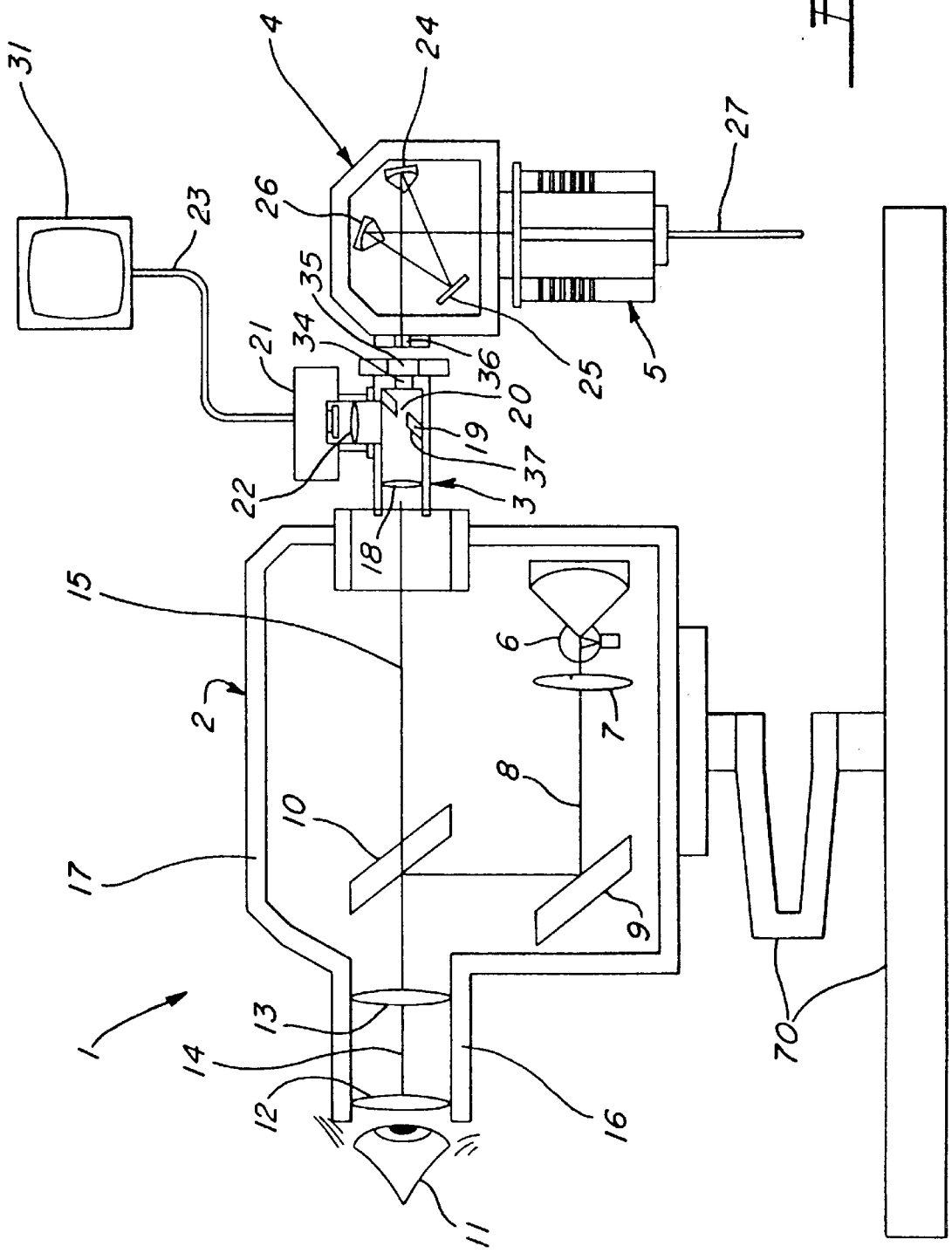
FIG. 1 is a schematic diagram of a first preferred embodiment of the spectroreflectometry oxygenation measurement device according to the present invention.

The preferred embodiment of the on-line, real-time spectroreflectometry oxygenation measuring device as illustrated in FIG. 1 is generally identified by the reference 1 and comprises a fundus camera 2, a camera-to-spectrograph interface 3, and a detector unit formed of a spectrograph 4 and a CCD (Charge Coupled Device) detector array 5.

The fundus camera 2 is supported by a mechanical frame 7 schematically illustrated in FIG. 1.

Figure 3:
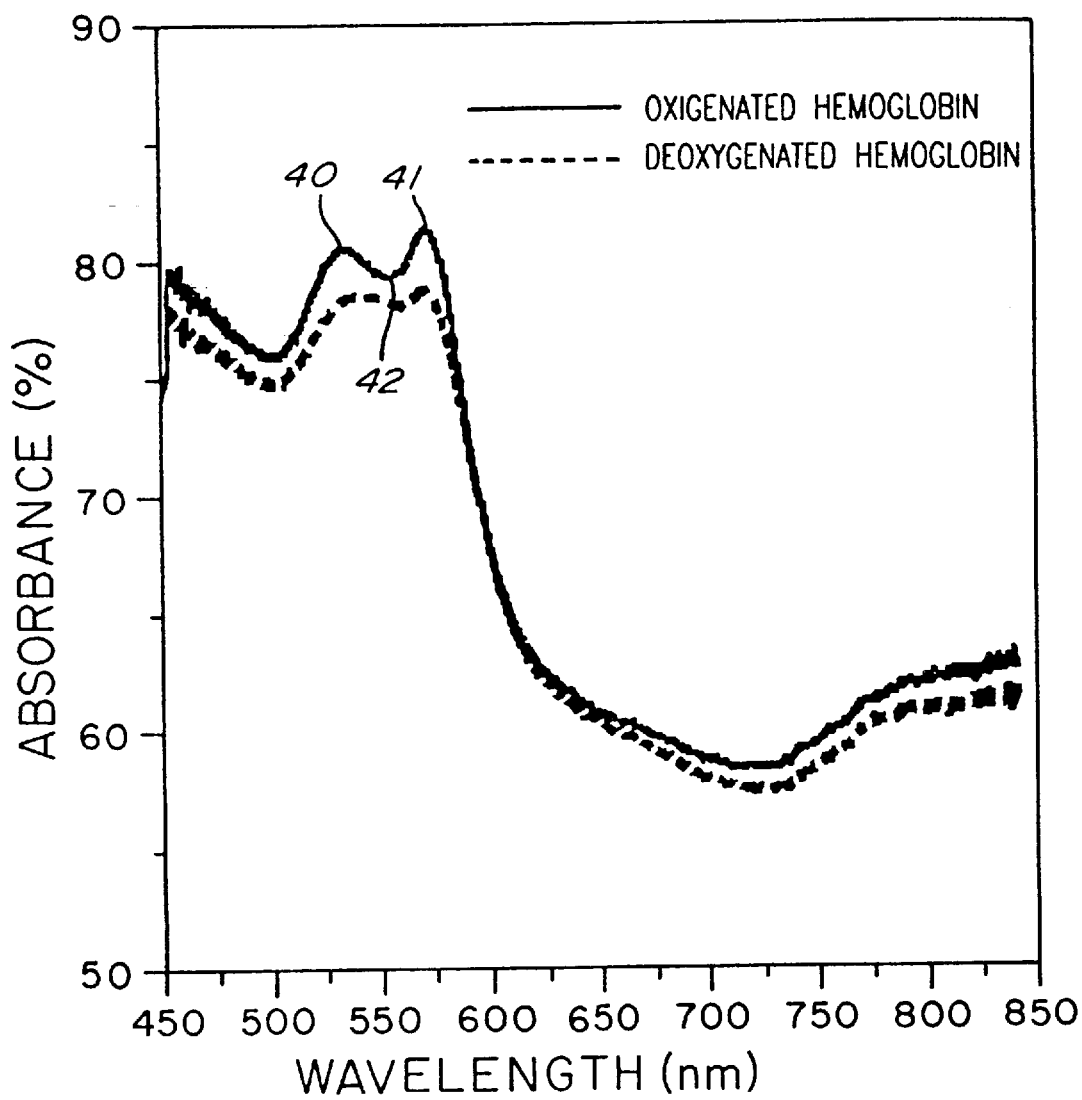
FIG. 3 is a graph of absorbance (%) versus wavelength (nm) indicative of the spectroreflectometry oxygenation measurement.

Still referring to FIG. 1, the fundus camera 2 comprises a light source 6 for producing light having a predetermined relatively wide spectral (frequency) bandwidth optimized for spectroreflectometry oxygenation measurement. More specifically, as illustrated in FIG. 3, the spectroreflectometry oxygenation measurement of hemoglobin and its derivatives such as oxyhemoglobin and carbonylhemoglobin is preferably conducted within a spectral bandwidth including the range of wavelengths comprised between 450 nm and 850 nm.

Light from the source 6 is propagated from the light source 6 to a region of the fundus of the patient's eye 11 by a first optical system. This first optical system comprises:
 a lens 7 to concentrate light generated by the source 6 into a light beam 8;
 45° mirror 9 and 45° beam splitter 10 to reflect the light beam 8 twice and transmit that light beam 8 to the patient's eye 11 along a linear trajectory 14; and
 a pair of lenses 12 and 13 mounted along the trajectory 14 to propagate the light beam 8 toward a region of the fundus of the patient's eye 11.

The intensity of the light beam 8 must be sufficiently low for being applied to the fundus of the patient's eye for the duration of the spectroreflectometry oxygenation measurement, without harming the patient's eye. For safety purposes, the light beam 8 of the spectroreflectometry oxygenation measurement device according to the invention has an intensity lower than 5 mW/cm$^2$, which is safe for on-line spectroreflectometry measurement involving exposure time as long as 6 minutes.

As can be seen in FIG. 1, the fundus camera 2 is formed with a housing 17 defining a cylindrical portion 16 in which the pair of lenses 12 and 13 are mounted. The cylindrical portion 16 defines with the lens 12 the objective of the fundus camera 2. Obviously, the patient places his (or her) eye 11 close to and in front of the lens 12 of the fundus camera 2 for on-line and real-time spectroreflectometry oxygenation measurement purpose. Preferably, the patient will place his (or her) mandible on a chin rest for positional stability of his (or her) eye 11.

Light beam 8 is reflected at least in part by the fundus of the patient's eye 11 to produce a reflected light beam 15 having a geometrical longitudinal axis (not shown). A second optical system propagates the reflected light beam along a predetermined propagation path 14 from the fundus of the patient's eye 11 to the detector unit (4, 5).

The second optical system comprises the pair of lenses 12 and 13, and the 45° beam splitter 10 to propagate the reflected light beam 15 from the fundus of the patient's eye 11 along the propagation path 14 toward the camera-to-spectrograph interface 3. 45° beam splitter 10 will cause no reflection of the reflected light beam 15 propagating along path 14 from the fundus of the patient's eye 11 to the interface 3.

The second optical system also comprises a lens 18 and a 45° mirror 19 of the camera-to-spectrograph interface 3. More specifically, the lens 18 propagates the reflected light beam 15 along the propagation path 14 toward the 45° mirror 19. Mirror 19 defines an angle of 45° and comprises a central, axial opening 20 having a predetermined diameter centered on the geometrical longitudinal axis of the reflected light beam 15. Of course, the central axial opening 20 will transmit to the detector unit (4, 5) only the axial central portion of the reflected light beam 15. The second optical system further comprises axial apertures such as 34, 35 and 36 provided in the housings of the camera-to-interface 3 and spectrograph 4 to enable the axial central portion of the reflected light beam 15 to reach the spectrograph 4.

Just a word to mention that the use of the axial central portion of the reflected light beam enables selection of a small precise area which is optimal for oxygenation measurement of specific structures such as the blindspot, arteries, veins, etc.

The mirror 19 comprises a light-reflecting annular surface 37 surrounding the axial central opening 20. The reflected light beam 15 comprises an axial peripheral portion surrounding the axial central portion and reflected by the light-reflecting annular surface 37 of the mirror. As illustrated in FIG. 1, the axial peripheral portion of the reflected light beam 15 is deviated by 90° by reflection on the light-reflecting annular surface 37 of the 45° mirror 19 to propagate toward a TV camera 21 through a lens 22 of the camera-to-spectrograph interface 3.

The image sensed by the TV camera 21 is displayed on a TV monitor 31 through a cable 23. This enables the operator to visualize the fundus of the patient's eye and the location of the axial central opening 20 on the fundus of the patient's eye, and therefore to select the small central area of interest where spectroreflectometry oxygenation measurement is desired.

The spectrograph 4 comprises a first concave mirror 24 having a generally elliptical cross section to receive the axial central portion of the reflected light beam 15 and to deflect this axial central light beam portion toward a generally planar diffraction grating 25. Diffraction grating 25 consists of an array of narrow slits or grooves which produce a large number of beams interfering with each other to produce a light spectrum. As it is well known to those of ordinary skill in the art, this light spectrum includes light components of the axial central portion of the reflected light beam 15 arranged in order of wavelength. The produced light spectrum is reflected by a second concave mirror 26 also having a generally elliptical cross section and deviated toward the CCD detector array 5.

In other words, the diffraction grating 25 separates the light components of different wavelengths within the range comprised between 450 nm and 850 nm. The intensities of the light components of different wavelengths of the light spectrum are detected and measured by the CCD detector array 5. For example, the CCD detector array 5 consists of a two-dimensional array comprising 1024 columns and 256 rows of light detectors, in which the rows are summed for each column to give a readout (output signal) indicative of the spectral content of the reflected light beam 15.

The readout (output signal) from the CCD detector array 5 is transmitted to a computer station (not shown) through an electric cable 27. This computer station is responsive to the measured intensities of the components of different wavelengths of the light spectrum for computing and displaying a graph of absorbance of the precise small area of the fundus of the patient's eye as a function of wavelength.

Figure 2:
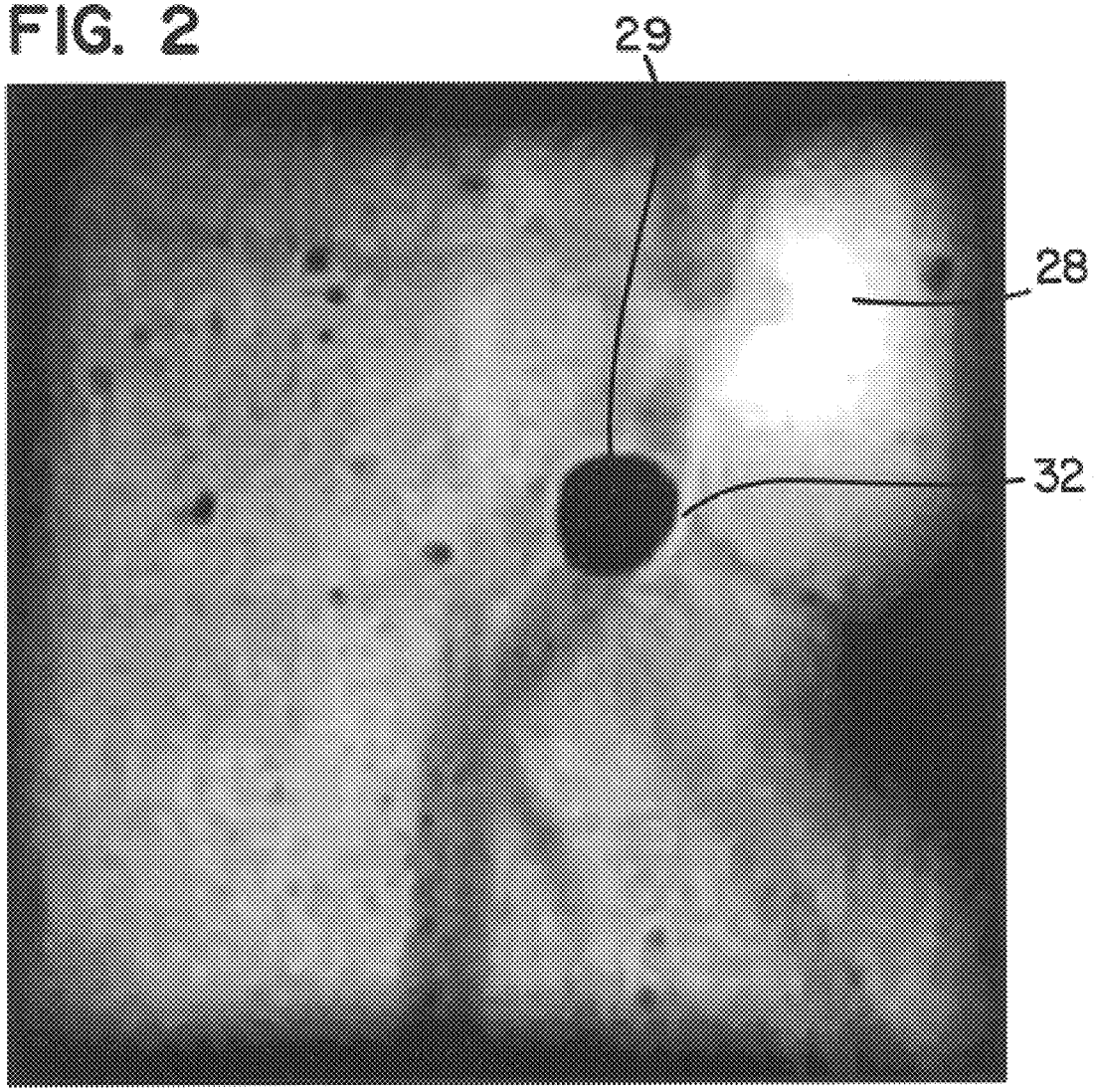
FIG. 2 is a photograph showing the fundus of a patient's eye as displayed on a TV monitor to enable the operator to apply a light beam to a desired location of the fundus of the patient's eye.

An example of image sensed by the TV camera 21 and displayed on the monitor 31 is shown (scale 1:1) on FIG. 2 of the appended drawings. More specifically, FIG. 2 shows the fundus 28 of the patient's eye and a black spot 29. The black spot 29 is produced by the axial opening 20 of the 45° mirror 19 and corresponds to the axial central portion of the reflected light beam 15 transmitted to the detector unit (spectrograph 4 and CCD detector array 5). Therefore, the black spot 29 indicates the precise small area of the fundus 28 of the patient's eye 11 which is analysed for oxygen content. Accordingly, the image on the monitor 31 will enable the operator to position as desired the black spot 29 on the fundus 28 of the patient's eye, by moving the fixation point of the patient relative to the axis of the propagation path 14.

For example, in the case of glaucoma, the oxygenation measurement can be taken in the region of the optic nerve. Those of ordinary skill in the art know that glaucoma identifies eye diseases characterized by an increase of the intraocular pressure, causing (a) hardening of the eyeball, (b) atrophy of the optic nerve accompanied by a physiologic excavation of the optic disk, (c) narrowing of the field of vision, and (d) a more or less important reduction of the visual acuity. In FIG. 2, the region of the optic nerve corresponds to the white region 32. In the case of glaucoma, oxygenation measurement is preferably conducted in a plurality of different positions of the black spot 29 in the region 32 and around that region 32.

It should however be kept in mind that the above example related to glaucoma is not intended to limit positioning of the black spot 29 on the fundus 28 of the patient's eye 11. In fact, the position of the black spot 29 on the fundus 28 of the patient's eye is selected in relation to the intended purpose of the spectroreflectometry oxygenation measurement.

FIG. 3 illustrates a graph of absorbance (%) versus wavelength (nm). Display of this graph by the monitor of the computer station will indicate to the operator the percentage of absorption of the different light wavelengths by the fundus 28 of the patient's eye 11. In particular, the amount of absorption between wavelengths 500–600 nm relative to the spectral bandwidth region between 650–700 nm represents the relative amount of hemoglobin content in the blood, while the characteristic peaks 40 and 41 and troughs 42 represent the relative oxygenation of the hemoglobin and thus the oxygen content. The greater the difference between the peaks 40 and 41 and the troughs 42 as shown in the two curves in FIG. 3 the more the blood is oxygenated. Similarly the zone between 700 and 850 nm can be analysed for the carbonylhemoglobin content.

The graph of FIG. 3 includes two curves to show the difference between results obtained when different levels of oxygenation are present: the curve "deoxygenated hemoglobin" corresponds to lack of oxygenation and the curve "oxygenated hemoglobin" corresponds to detection of oxygenation.

In the range of wavelengths 450–600 nm, the shape of the curve between the two peaks 40 and 41 is indicative of the ratio between "deoxygenated hemoglobin" and "oxygenated hemoglobin. Model curves can then be used to evaluate the degree of oxygenation.

In the range of wavelengths 600–850 nm, the presence of a peak at a particular wavelength may indicate the presence of a particular substance and/or a corresponding contamination, to thereby identify and diagnose a given pathology.

Also, the range of wavelengths 450–850 nm further presents the advantage of including wavelengths to which each portion of a patient's eye are transparent. In other words, all the portions of the patient's eye will be transparent to at least some wavelengths of the range 450–850 nm whereby spectroreflectometry oxygenation measurements can be made in any region of the patient's eye including the pigmented regions.

It should also be kept in mind that, although a graph is shown as non limitative example in FIG. 3 of the appended drawings, tables and/or other data related to the spectroreflectometry oxygenation measurement can be displayed on the monitor of the computer station (not shown) connected to the CCD detector array 5 through the cable 27.

Figure 4:
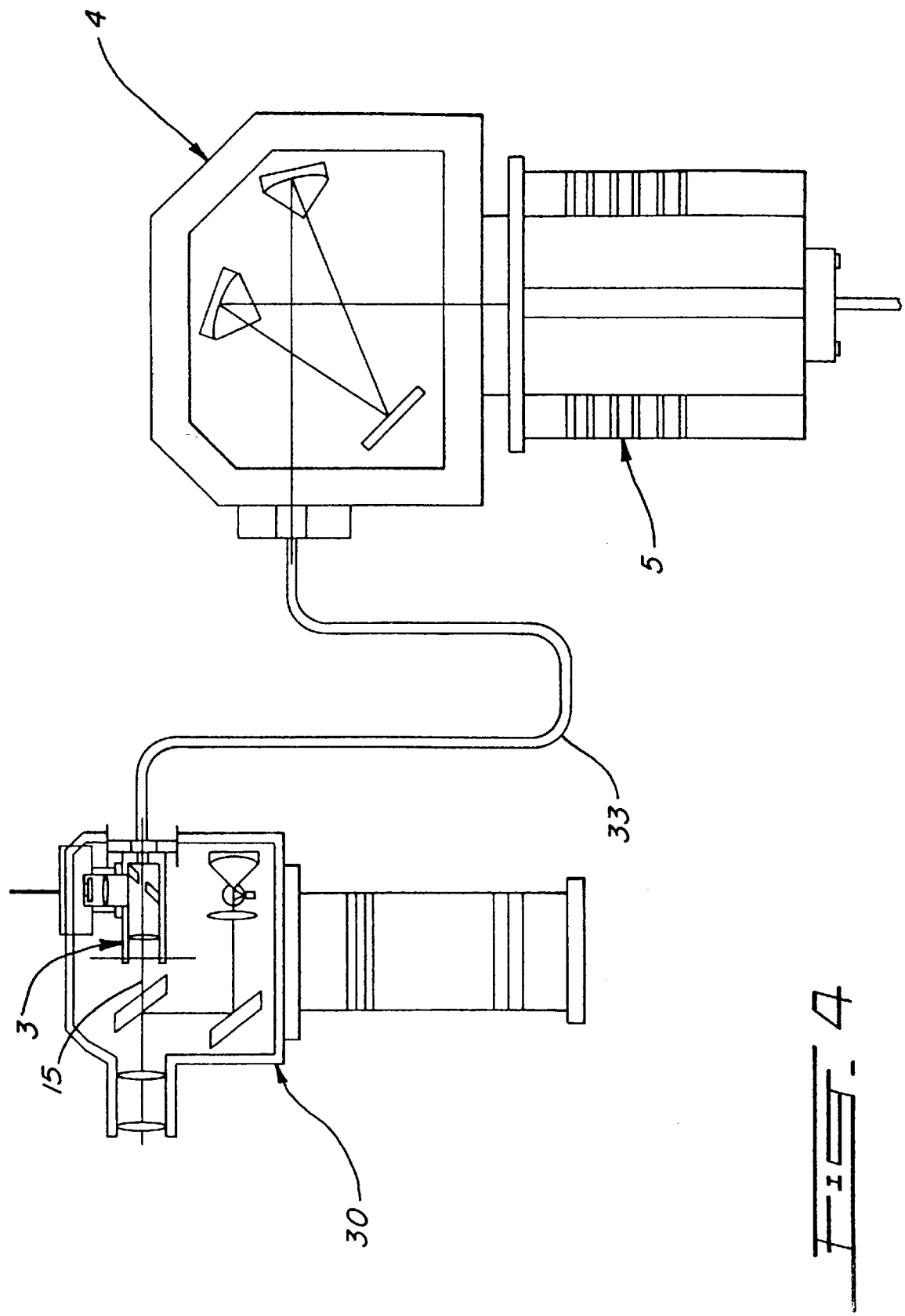
FIG. 4 is a schematic diagram of a second preferred embodiment of the spectroreflectometry oxygenation measurement device according to the present invention.

In the preferred embodiment of FIG. 4, the camera-to-spectrograph interface 3 has been incorporated into a portable, hand-held fundus camera 30 (ophthalmoscope). The second optical system then comprises an optical fiber 33 to connect the output of the camera-to-spectrograph interface 3 to the input of the spectrograph 4, i.e to transmit the axial central portion of the reflected light beam 15 from the camera-to-spectrograph interface 3 to the spectrograph 4. Otherwise, the structure and operation of the spectroreflectrometry oxygenation measurement device is unchanged with respect to the embodiment of FIG. 1.

The embodiment of FIG. 1, including a fixed fundus camera 2, is suitable for use with persons capable of moving and to place their mandible on a chin rest. The embodiment of FIG. 4, including a portable fundus camera 2, is suitable for incapacitated persons, for example persons sitting in a wheelchair, confined to bed or transported in an ambulance.

Accordingly, the spectroreflectometry oxygenation measurement device according to the invention is non-invasive and capable of performing, on-line and in real time, an in-vivo spectroreflectometry oxygenation measurement on the fundus of the patient's eye. For that purpose, the on-line spectroreflectometry oxygenation measurement device (a) uses a single light beam 8 having a spectral bandwidth including all the wavelengths (450 nm–850 nm) useful for spectroreflectometry oxygenation measurement and transmitted to a given region of the fundus of the patient's eye, and (b) transmits to the spectrograph 4 the most useful information of the light beam 15 reflected from the fundus of the patient's eye (central portion of the light beam 15) for spectroreflectometry oxygenation measurement purpose through the central axial hole 20 of the 45° mirror 19.

Also, the non-invasive spectroreflectometry oxygenation measurement device uses a display system including a TV camera 21 and monitor 31 providing for direct visualization of the fundus of the patient's eye coupled with a spectroreflectometry detector unit (spectrograph 4 and CCD detector array 5) providing for on-line, real-time oxygenation measurement over a large spectral bandwidth. This results in characterizing absorbance at precise locations of the spectrum corresponding to the unique characteristic of the oxygen content in the blood. With the same spectroreflectometry oxygenation measurement device, it is also possible to measure hemoglobin and most of its derivatives (e.g. oxyhemoglobin, carbonyihemoglobin, etc.).

The range of potential applications of the spectroreflectometry oxygenation measurement device according to the invention is extremely large. The diagnostic potential of directly measuring oxygenation in the eye, on-line and in real time, for visual pathologies is obvious. The medical assessment of almost all visual pathologies such as diabetic retinopathy, glaucoma, macular degeneration, retinal detachment, rod/cone dystrophies, etc., including direct consequences of laser surgery in treatment would benefit from using such a procedure. In fact, the advantage of such a procedure goes beyond the assessment of visual pathologies but expands to the medical management of toxicity, effects of medication, vascular diseases in general, and many other areas. Furthermore, the impact of on-line measurement of hemoglobin and oxygen of patients under surgery or premature babies is of great medical significance.

With the spectroreflectometry oxygenation measurement device, one just needs to stop breathing for several seconds to see the changes of oxygenation in real time, for example on the graph of FIG. 3. The effect is reversed when the subject starts breathing again. The same phenomenon is produced by applying a slight pressure to the eye to reduce the blood flow and oxygen content within the eye.

The inventors have conducted a study comparing the oxygenation changes in the eye with blood pressure changes and have compared these changes directly with oxygenation changes in the arm caused by applying pressure. The results of this study are perfectly clear and consistent. All subjects show a decrease of oxygen with increase pressure both in the eye and the arm. In fact, the same subjects show similar pattern changes in the eye and in the arm. This demonstrates that on-line and real time spectroreflectometry oxygenation measurement on the fundus of the eye is of great significance.

Although the present invention has been described hereinabove by way of preferred embodiments thereof, these embodiments can be modified at will, within the scope of the appended claims, without departing from the spirit and nature of the subject invention.

What is claimed is:

1. A spectroreflectometry oxygenation measuring device, comprising:

a light source for producing a light beam having a predetermined spectral bandwidth;

a first optical system for propagating the light beam from the light source to a region of the fundus of a patient's eye, the light beam being reflected at least in part by the fundus of the patient's eye to produce a reflected light beam having a geometrical longitudinal axis;

a detector unit for detecting the spectral content of the reflected light beam and for producing a signal indicative of the spectral content of said reflected light beam; and a second optical system for propagating the reflected light beam along a predetermined propagation path from the fundus of the patient's eye to the detector unit, wherein said second optical system comprises means for transmitting to the detector unit only an axial central portion of the reflected light beam corresponding to a small precise area of the fundus of the patient's eye where a spectroreflectometry oxygenation measurement is desired.

2. The spectroreflectometry oxygenation measuring device as recited in claim 1, wherein the predetermined spectral bandwidth includes a range of wavelengths comprised between 450 nm and 850 nm.

3. The spectroreflectometry oxygenation measuring device as recited in claim 1, wherein the reflected light beam comprises an axial peripheral portion surrounding the axial central portion, and wherein the second optical system further comprises means for transmitting the axial peripheral portion of the reflected light beam to a display system enabling an operator to visualize the fundus of the patient's eye and the location of the light beam on the fundus of the patient's eye.

4. The spectroreflectometry oxygenation measuring device as recited in claim 3, wherein:

the means for transmitting to the detector unit only an axial central portion of the reflected light beam comprises an axial opening in a mirror defining an angle of 45° with the predetermined propagation path, the axial opening having a predetermined diameter centered on the geometrical longitudinal axis of the reflected light beam for transmitting to the detector unit only the axial central portion of said reflected light beam; and the means for transmitting the axial peripheral portion of the reflected light beam to a display system comprises a light-reflecting surface of the mirror surrounding the axial opening for deviating said axial peripheral portion of the reflected light beam toward the display system.

5. The spectroreflectometry oxygenation measuring device as recited in claim 4, wherein the display system comprises means for displaying an image of the fundus of the patient's eye including a black spot indicating said region of the fundus of the patient's eye to which the light beam from the light source is applied, wherein said black spot is produced by the axial opening of the mirror and corresponds to the axial central portion of the reflected light beam transmitted to the detector unit.

6. The spectroreflectometry oxygenation measuring device as recited in claim 1, in which said detector unit comprises:

a spectrograph responsive to the axial central portion of the reflected light beam to produce a light spectrum including light components of the axial central portion of the reflected light beam arranged in order of wavelengths; and an array of detectors for measuring intensities of the light components of different wavelengths of the light spectrum.

7. The spectroreflectometry oxygenation measuring device as recited in claim 6, further comprising means responsive to the measured intensities of the light components of different wavelengths of the light spectrum for computing and displaying a graph of absorbance of the fundus of the patient's eye as a function of wavelength within said predetermined spectral bandwidth.

8. The spectroreflectometry oxygenation measuring device as recited in claim 1, comprising a portable fundus camera incorporating the light source, the first optical system and a portion of the second optical system, and wherein said second optical system further comprises an optical fiber for transmitting the axial central portion of the reflected light beam from the portable fundus camera to the detector unit.

9. The spectroreflectometry oxygenation measuring device as recited in claim 1, wherein the light beam produced by the light source has an intensity sufficiently low for being applied to the fundus of the patient's eye for the duration of the spectroreflectometry oxygenation measurement while causing no harm to the patient's eye.

10. The spectroreflectometry oxygenation measuring device as recited in claim 9, wherein the light beam from the light source has an intensity substantially equal to daylight.

11. A spectroreflectometry oxygenation measuring method comprising the steps of:

producing a light beam having a predetermined spectral bandwidth by means of a light source;

propagating the light beam toward a region of the fundus of a patient's eye;

reflecting at least in part the light beam on the fundus of the patient's eye to produce a reflected light beam having a geometrical longitudinal axis;

by means of a detector unit, detecting the spectral content of the reflected light beam and producing a signal indicative of the spectral content of said reflected light beam; and propagating the reflected light beam along a predetermined propagation path from the fundus of the patient's eye to the detector unit, wherein said step of propagating the reflected light beam comprises transmitting to the detector unit only an axial central portion of the reflected light beam corresponding to a small precise area of the fundus of the patient's eye where a spectroreflectometry oxygenation measurement is desired.

12. The spectroreflectometry oxygenation measuring method as recited in claim 11, wherein the step of producing a light beam having a predetermined spectral bandwidth comprises producing a light beam including a range of wavelengths comprised between 450 nm and 850 nm.

13. The spectroreflectometry oxygenation measuring method as recited in claim 11, wherein the reflected light beam comprises an axial peripheral portion surrounding the axial central portion, and wherein the step of propagating the reflected light beam further comprises transmitting the axial peripheral portion of the reflected light beam to a display system enabling an operator to visualize the fundus of the patient's eye and the location of the axial central portion of the light beam on the fundus of the patient's eye.

14. The spectroreflectometry oxygenation measuring method as recited in claim 13, wherein the step of transmitting the axial peripheral portion of the reflected light beam to a display system comprises deviating said axial peripheral portion of the reflected light beam toward the display system.

15. The spectroreflectometry oxygenation measuring method as recited in claim 13, further comprising the step of displaying an image of the fundus of the patient's eye including a black spot indicating said small precise area of the fundus of the patient's eye.

16. The spectroreflectometry oxygenation measuring method as recited in claim 11, in which the steps of detecting the spectral content of the reflected light beam and producing a signal indicative of the spectral content of the reflected light beam comprise:

producing a light spectrum including light components of the axial central portion of the reflected light beam arranged in order of wavelengths; and measuring intensities of the light components of different wavelengths of the light spectrum.

17. The spectroreflectometry oxygenation measuring method as recited in claim 16, further comprising the steps of:

computing from the measured intensities of the light components of different wavelengths of the light spectrum a graph of absorbance of the small precise area of the fundus of the patient's eye as a function of wavelength within said predetermined spectral bandwidth; and displaying said graph.

18. The spectroreflectometry oxygenation measuring method as recited in claim 11, wherein the step of producing a light beam having a predetermined spectral bandwidth comprises producing a light beam having an intensity sufficiently low for being applied to the fundus of the patient's eye for the duration of the spectroreflectometry oxygenation measurement while causing no harm to the patient's eye.

19. The spectroreflectometry oxygenation measuring method as recited in claim 11, wherein the step of producing a light beam having a predetermined spectral bandwidth comprises producing a light beam having an intensity substantially equal to daylight.

* * * * *